US00PP14412P29

(12) United States Plant Patent
Gerdts et al.

(10) Patent No.: US PP14,412 P2
(45) Date of Patent: Dec. 23, 2003

(54) NECTARINE TREE NAMED 'BURNECTTWELVE'

(50) Latin Name: *Prunus persica*
Varietal Denomination: Burnecttwelve

(75) Inventors: Timothy J. Gerdts, Kingsburg, CA (US); John K. Slaughter, Clovis, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 8 days.

(21) Appl. No.: 10/334,348

(22) Filed: Dec. 30, 2002

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of nectarine tree (*Prunus persica* sub species *nuciperisica*), denominated varietally as 'Burnecttwelve', and which produces an attractively colored yellow-fleshed, clingstone nectarine, which is mature for harvesting and shipment approximately May 19 to May 28 under ecological conditions prevailing in the San Joaquin Valley of central California.

1 Drawing Sheet

BACKGROUND OF THE NEW VARIETY

The present invention relates to a new, novel and distinct variety of nectarine tree, *Prunus persica* (subspecies *nuci-persica*), and which has been denominated varietally as 'Burnecttwelve'.

ORIGIN

The present variety of nectarine tree resulted from an on-going program of fruit and nut tree breeding. The purpose of this program is to improve the commercial quality of deciduous fruit and nut varieties and rootstocks by creating and releasing promising selections of prunus, malus and regia species. To this end we make both controlled and hybrid cross pollinations each year in order to produce seedling populations from which improved progenies are evaluated and selected.

The seedling 'Burnecttwelve' was originated by us from a population of seedlings grown in our experimental orchards which are located near Fowler, Calif. The seedlings, grown on their own roots, were the result of a controlled cross of the yellow-fleshed 'Arctic Star' nectarine tree (U.S. Plant Pat. No. 9,332), which was used as the pollen parent, and the yellow fleshed nectarine tree, 'Crimson Baby', (unpatented) which was used as the seed parent. One seedling designated as E45.002, which is the present variety, exhibited especially desirable characteristics. This promising variety was marked for subsequent observation. After the 1999 growing season, the new variety nectarine tree was selected for advanced evaluation and repropagation.

ASEXUAL REPRODUCTION

Asexual reproduction of this new and distinct variety of nectarine tree was accomplished by budding to 'Nemaguard Rootstock' (non-patented). This was performed by us in our experimental orchard located near Fowler, Calif. Subsequent evaluations have shown those asexual reproductions run true to the original tree. All characteristics of the original tree and its fruit were established and appear to be transmitted through succeeding asexual propagations. We have observed fruit for the past 3 successive years from approximately 15 propagated trees.

SUMMARY OF THE VARIETY

'Burnecttwelve' is a new and distinct variety of nectarine tree, which is of large size, and which has vigorous growth. The new variety of nectarine tree is also a regular, and productive bearer of relatively large, firm, yellow fleshed, sub-acidic, clingstone fruit which has both a good flavor and eating quality. This new and novel tree has a medium to low chilling requirement of approximately 500 hours. The tree also produces relatively uniformly sized fruit throughout the tree. The fruit further has a high degree of red skin coloration, and a firm flesh. The fruit of the present variety also appears to have good handling and shipping qualities. In addition to the foregoing, the 'Burnecttwelve' nectarine tree bears fruit which are ripe for commercial harvesting and shipment on approximately May 19 to May 23 under the ecological conditions prevailing in the San Joaquin Valley of central California. In relative comparison with the pollen parent 'Arctic Star' nectarine tree, the 'Burnecttwelve' Nectarine tree produces fruit which ripen about 7 to 9 days earlier at the same geographical location.

BRIEF DESCRIPTION OF THE DRAWING

The accompanying drawing, which is provided, is a color photograph of the present variety. The photograph depicts two whole mature fruit, and one fruit dissected in the equatorial plane thereby exposing the flesh and the pit. Further, fruit flesh has been removed to expose a single characteristic pit. A vegetative shoot bearing typical leaves is shown. The external coloration of the fruit, as shown, is sufficiently matured for harvesting and shipment. The colors in this photograph are as nearly true as is reasonably possible in a color representation of this type. Due to chemical development, processing and printing, the leaves and fruit depicted in these photographs may or may not be accurate when compared to an actual specimen. For this reason, future color references should be made to the color plates (Royal Horticultural Society) and descriptions provided.

DETAILED DESCRIPTION

Referring more specifically to the pomological details of this new and distinct variety of nectarine tree, the following has been observed during the fourth fruiting season under the ecological conditions prevailing at orchards which are located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally — Considered medium-large when compared to other common commercial nectarine cultivars ripening in the early season of maturity. The tree of the present variety was pruned to a height of approximately 295.0 cm to 320.0 cm at maturity.

*Vigor.*—Considered vigorous. The present variety grew from about 145.0 cm to about 154.0 cm in height during the first growing season. The variety was pruned to a height of approximately 134.6 cm during the first dormant season, and primary scaffolds were then selected for the desired tree structure.

*Productivity.*—Productive. Fruit set varies from about twice to several times more than the desired crop load. Fruit set is spaced by thinning to allow the remaining fruit to develop into the desired market sized fruit. The number of the fruit set varies with climatic conditions and the prevailing cultural practices during the bloom period, and is therefore not distinctive of the variety.

*Bearer.*—Regular. Fruit set has been heavy, and thinning was necessary during the past 4 years.

*Form.*—Upright, and pruned to a vase shape.

*Density.*—Medium dense. It has been discovered that pruning the branches from the center of the tree to obtain a resulting vase-like shape appears to allow air movement and appropriate amounts of sunlight to enhance fruit color and renewal of fruiting wood throughout the tree.

*Hardiness.*—The present tree was grown and evaluated in USDA Hardiness Zone 9. Winter chilling requirements are approximately 500 hours below 7.0 degrees C. The present variety appears to be hardy under typical central San Joaquin Valley climatic conditions.

Trunk:

*Diameter.*—Approximately 12.8 cm in diameter when measured at a distance of approximately 15.24 cm above the soil level, at the end of the fourth growing season.

*Bark texture.*—Considered moderately rough, with numerous folds of papery scarfskin being present.

*Lenticels.*—Numerous flat, oval lenticels are present. The lenticels range in size from approximately 4.0 to about 5.0 millimeters in width, and from 1.0 to about 2.0 millimeters in height.

*Lenticel color.*—Considered an Orange Brown, (RHS Greyed Orange Group 166 C).

*Bark coloration.*—Variable, but it is generally considered to be gray-brown, (RHS Greyed Orange Group 174 A).

Branches:

*Size.*—Considered medium for the variety.

*Diameter.*—Average as compared to other nectarine tree varieties. The branches have a diameter of about 7.1 centimeters when measured during the fourth year following grafting.

*Surface texture.*—Average, and appearing furrowed on wood which is several years old.

*Crotch angles.*—Primary branches are considered variable between about 46 to about 52 degrees from the horizontal axis. This characteristic is not considered distinctive of the variety, however.

*Current season shoots.*—Surface texture — Substantially glabrous.

*Internode length.*—Approximately 2.3 to 2.4 cm.

*Color of mature branches.*—Medium brown, (RHS Greyed Orange 176 C).

*Current seasons shoots.*—Color — Light green, (RHS Yellow Green Group N144 B). The color of the new shoot tips is considered a bright and shiny green (RHS Yellow Green Group 143 B).

Leaves:

*Size.*—Considered medium-large for the species. Leaf measurements have been taken from vigorous, upright, current-season growth at approximately mid-shoot.

*Leaf length.*—Approximately 157.0 to about 164.0 millimeters.

*Leaf width.*—Approximately 30.0 to about 35.0 millimeters.

*Leaf base shape.*—Slightly oblique relative to the leaf longitudinal axis.

*Leaf form.*—Lancelolate.

*Leaf tip form.*—Acuminate.

*Leaf color.*—Upper Surface — Dark green, (approximately RHS Green Group 139 B).

*Leaf texture.*—Glabrous.

*Leaf color.*—Lower Surface — Medium green, (RHS Green Group 141 C).

*Leaf venation.*—Pinnately veined.

*Mid-vein.*—Color — Light yellow green, (RHS Yellow Green Group 149 B).

*Leaf margins.*—Slightly undulating.

*Form.*—Considered crenate, occasionally doubly crenate.

*Uniformity.*—Considered generally uniform.

*Leaf petioles.*—Size — Considered medium long. Length — About 8.0 to about 10.0 mm. Diameter — About 1.5 to about 2.0 mm. Color — Pale green, (RHS Yellow Green Group N144 A).

*Leaf glands.*—Size — About 1.0 mm in height, and about 2.0 mm in width. Number — Generally one per side, occasionally two per side may be found. Type — Reniform, and considered reasonably unappressed to the petiole margin. The leaf glands are considered moderately small. Color — Medium brown, (RHS Greyed Brown Group N199 C).

*Leaf stipules.*—Size — Medium for the variety. Number — Typically 2 per leaf bud, and up to 6 per shoot tip. Form — Lanceolate, and having a serrated margin. Color — Green, (RHS Green Group 141 B) when young, but graduating to a brown color, (RHS Greyed Orange Group 166 C) with advancing senescence. The stipules are considered to be early deciduous.

Flowers:

*Flower buds.*—Generally — The floral buds, depending upon the stage of development, are approximately 5.0 millimeters wide; and about 7.0 millimeters long; conic in form; and slightly appressed relative to the bearing shoot.

*Flower buds.*—Color — The bud scales are reddish-brown, (approximately RHS Greyed Purple Group 183 A).

*Hardiness.*—The flower buds are considered hardy under typical central San Joaquin Valley climatic conditions. No winter injury has been noted during the last several years of evaluation in the central San Joaquin Valley. The present variety has not been intentionally subjected to drought, or heat stress, therefore this information is not available.

*Date of first bloom.*—Feb. 23, 2002.

*Blooming time.*—Considered mid-season in relative comparison to other commercial nectarine cultivars grown in the central San Joaquin Valley. Date of full bloom was observed on Feb. 28, 2002. The date of bloom varies slightly with climatic conditions and prevailing cultural practices.

*Duration of bloom.*—Approximately 9 days. This characteristic may vary slightly with climatic conditions.

*Flower type.*—The variety is considered to have a showy type flower.

*Flower size.*—Flower diameter at full bloom is approximately 40.0 to about 45.0 millimeters.

*Bloom quantity.*—Considered abundant.

*Flower bud frequency.*—Normally 1 to 2 appear per node. Rarely 3 per node may be found.

*Petal size.*—Generally — Considered large for the species. Length — Approximately 18.0 to about 21.0 millimeters. Width — Approximately 12.0 to about 15.0 millimeters.

*Petal form.*—Broadly ovoid.

*Petal count.*—Nearly always 5.

*Petal texture.*—Glabrous.

*Petal color.*—Light pink, (RHS Red Purple Group 65 B), to a medium pink, (RHS Red Purple Group 68 C).

*Fragrance.*—Slight.

*Petal claw.*—Form — The claw is generally considered to be truncate, and has a small size when compared to other nectarine tree varieties. Length — Approximately 6.0 to about 7.0 millimeters. Width — Approximately 5.0 to about 6.0 millimeters.

*Petal margins.*—Generally considered variable, from nearly smooth, to moderately undulate and ruffled, especially apically.

*Petal apex.*—Generally — The petal apices appear entire and without an apical groove.

*Flower pedicel.*—Length — Considered medium-long, and having an average length of approximately 3.0 to 4.0 millimeters. Diameter — Considered average, approximately 2.0 millimeters. Color — A medium brown, (RHS Grey Brown Group 199 A).

*Floral nectaries.*—Color —A Dull orange red, (RHS Greyed Orange Group 167 A).

*Calyx.*—Surface texture — Generally glabrous. Color — A dull red, (approximately RHS Greyed Red Group 181 C).

*Sepals.*—Surface Texture — The surface has a short, fine pubescent texture. Size — Average, and ovate in form. Color — A pale purple, (approximately RHS Purple Group N77C).

*Anthers.*—Generally — Average in size. Color — Reddish purple dorsally, (approximately RHS Greyed Purple Group 187 B).

*Pollen production.*—Pollen is abundant, and has a yellow color, (approximately RHS Yellow Orange Group 16 A).

*Filaments.*—Size — Variable in length, approximately 13.0 to about 17.0 mm. Color — Considered a pale pink, (RHS Red Purple Group 62 D).

*Pistil.*—Number — Usually 1, rarely 2. Size — Average. Length — Approximately 18.0 to about 20.0 millimeters including the ovary. Color — Considered a very pale green, (approximately RHS Yellow Green Group 154 D). Surface Texture — The variety has a long glabrous pistil.

Fruit:

*Maturity when described.*—Firm ripe condition (shipping ripe). Date of first picking — May 19, 2002. Date of last picking — May 28, 2002. The date of harvest may vary slightly with the prevailing climatic conditions.

*Size.*—Generally — Considered relatively large, and uniform.

*Average cheek diameter.*—Approximately 76.0 to about 80.0 millimeters.

*Average axial diameter.*—Approximately 72.0 to about 78.0 millimeters.

*Typical weight.*—Approximately 220.0 grams. This fruit weight is dependent upon the cultural practices employed and therefore is not distinctive of the present variety.

*Fruit form.*—Generally — Moderately oblate. The fruit is generally considered uniform in its symmetry.

*Fruit suture.*—Shallow, and extending from the base to apex. No apparent callousing or stitching exists along the suture line.

*Suture.*—Color — The background color appears to be a light yellow, (approximately RHS Yellow Group 6 C) and occasionally having some red coloration, (approximately RHS Red Group 46 B).

*Ventral surface.*—Form — Slightly indented.

*Apex.*—Rounded.

*Base.*—Retuse.

*Stem cavity.*—Shape — Rounded, and relatively shallow. The average depth of the stem cavity is about 1.45 cm. Average width of the stem cavity is about 2.55 cm.

*Fruit skin.*—Thickness — Considered medium in thickness, and tenacious to the flesh. Texture — Short, fine pubescence is present. Taste — Non-astringent. Tendency to crack — A low incidence of cracking has been observed. Skin russetting is occasionally observed on some fruit which are exposed to extreme weather conditions.

*Color.*—Blush Color — This red blush color is variable from a reddish orange, (approximately RHS Red Group 40 A), to a dark red, (approximately RHS Red Group 46 B). The blush color ranges from about 75% to about 95% of the entire fruit surface depending upon the sunlight exposure and the prevailing growing conditions. Ground Color — Generally, a light yellow, (approximately RHS Yellow Group 6 C).

*Fruit stem.*—Size — Moderate in length, approximately 5.0 to about 7.0 millimeters. Diameter — Approximately 2.0 to 3.0 millimeters.

*Color.*—Pale yellow-green, (approximately RHS Greyed Orange Group 163 C).

*Flesh.*—Ripening — Considered even. Texture — Firm, and dense, yet considered melting. Fibers —

Few, small, and tender. Aroma — Very slight. Eating quality — Considered very good. Flavor — Considered sweet and having a very low acid to sub-acidic flavor. The flavor is considered both pleasant and balanced. Juice Production — Moderate. Brix — About 16.0 degrees. This characteristic varies slightly with the number of fruit per tree, prevailing cultural practices, and the surrounding climatic conditions. Flesh Color — Pale yellow, (approximately RHS Yellow-Orange Group 18 B).

Stone:

*Type.*—Clingstone.

*Size.*—Considered medium large for the variety. The stone size varies with the crop load and the tree vigor, and is therefore not characteristic of the variety.

*Length.*—Average, about 27.5 to about 29.0 millimeters.

*Width.*—Average, about 23.0 to about 25.0 millimeters.

*Diameter.*—Average, about 18.0 to about 21.0 millimeters.

*Form.*—Obovoid.

*Base.*—The stone base is usually oblique relative to the stone's vertical axis.

*Apex.*—Shape — The stone apex is raised, and has an acute, protruding tip.

*Stone surface.*—Surface Texture — Irregularly furrowed toward the apex, and pitted toward the base. The stone exhibits substantial grooving laterally. Substantial grooving over the apical shoulders is evident. Surface pitting is more prominent generally, and noted more frequently in the mid-section of the stone. Ridges — The surface texture varies from sharp to rounded. Ventral Edge — Width — Considered medium in size, and having a dimension of approximately 2.0 to about 4.0 millimeters when measured at mid-suture. The wings are most prominent over the suture line. Dorsal Edge — Shape — Full, heavily grooved, and having jagged edges. The dorsal edge is significantly eroded over the apical shoulder.

*Stone color.*—The color of the dry stone is a pale yellow, (approximately RHS Orange White Group 159C).

*Tendency to split.*—Occasional splits have been noted.

*Kernel.*—Size — The kernel is considered small. Form — Considered irregular in shape and immature at fruit ripening. Pellicle — Pubescence has not developed at fruit senescence. Color — The kernel is gelatinous and generally translucent at fruit maturity.

*Use.*—The subject variety 'Burnecttwelve' is considered to be a Nectarine tree of the early season maturity, and which produces fruit which are considered firm, attractively colored, and which are useful for both local and long distance shipping.

*Keeping quality.*—Excellent. Fruit has stored well up to 25 days after harvest at 1.0 degree Celsius.

*Shipping quality.*—Good. The fruit of the present variety showed minimal bruising of the flesh or skin damage after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree substantially as illustrated and described, and which is characterized principally as to novelty by producing an attractively colored yellow-fleshed, clingstone nectarine which is mature for harvesting and shipment approximately May 19 to May 28 under the ecological conditions prevailing in the San Joaquin Valley of central California.

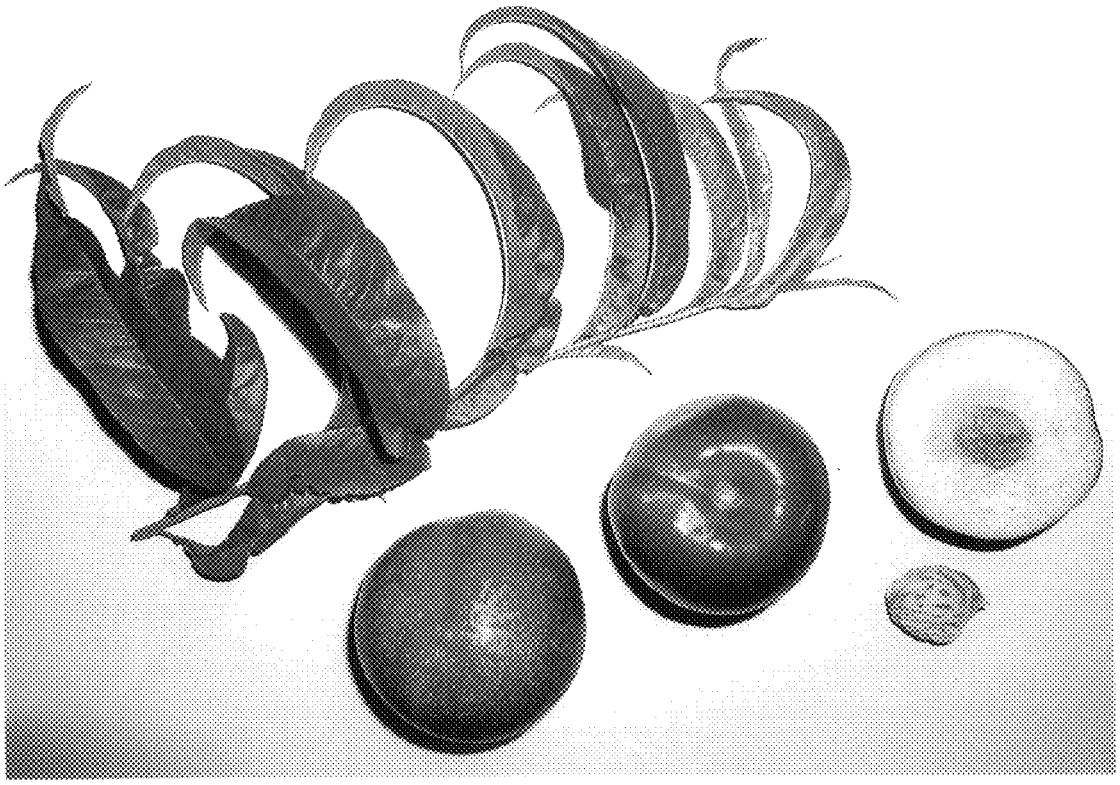

* * * * *